United States Patent [19]
Kreutner et al.

[11] Patent Number: 5,006,560
[45] Date of Patent: Apr. 9, 1991

[54] USE OF GABA-B SELECTIVE AGONISTS AS ANTI-TUSSIVE AGENTS

[75] Inventors: William Kreutner, West Caldwell; Donald Bolser, Bedminster; Richard Chapman, Somerville; Sultan Aziz, Woodcliff Lake, all of N.J.

[73] Assignee: Schering Corporation, Kenilworth, N.J.

[21] Appl. No.: 454,786

[22] Filed: Dec. 20, 1989

[51] Int. Cl.$^5$ ............... A61K 31/66; A61K 31/195
[52] U.S. Cl. ............................ 514/114; 514/567; 514/850
[58] Field of Search ............ 514/649, 114, 850, 567; 562/449; 560/20

[56] References Cited

U.S. PATENT DOCUMENTS 3,471,548 10/1969 Keberle et al. ............... 560/38

OTHER PUBLICATIONS

Nosalova et al. (1987), GABA-ergic Mechanisms in the Central Control of Cough, *Acta Physiologica Hungarica*, 70: 189–194, (1987).
Bowery et al., "Bicuculline-Insensitive GABA Receptors on Peripheral Autonomic Nerve Terminals", *Eur. J. Pharmacol.* 71: 53–70, (1981).
Hills et al., (1989) 3APPA–A Potent, Selective GABA-B Receptor Agonist in the GP Ileum and Rat Anococcygeus Muscle, *Br. J. Pharmacol.* 97: 1292–1296.
J. Bormann, Trends Neuroscience 11, pp. 112–116, (1988).
N. Bowery et al., Tips reviews 10, 401–407 (1989).
Hughes et al., Br. J. Pharmac. 53, 371–381, (1975).
Bowery et al., Br. J. Pharmac. 78, 191–206, (1983).
Hedner et al., NS Arch. Pharmacol. 317, 315–320, (1981).
Hedner et al., Eu. J. of Pharmacol., 81, 603–611 (1982).
Hedner et al., Jour. Neural Transmission, 59, 105–118, (1984).
Maggi et al., Br. J. Pharmac. 97, 103–110, (1989).
Giotti et al., Br. J. Pharmac. 78, 469–478 (1983).
Krantis et al., Eur. J. Pharmac., 141, 291–298 (1987).

*Primary Examiner*—Douglas W. Robinson
*Assistant Examiner*—Gary E. Hollinden
*Attorney, Agent, or Firm*—Matthew Boxer; James R. Nelson

[57] ABSTRACT

A method for treating cough in a mammal comprising administering to said mammal an anti-tussive effective amount of a GABA-B selective agonist such as

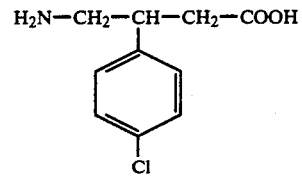

is described.

5 Claims, 3 Drawing Sheets

USE OF GABA-B SELECTIVE AGONISTS AS ANTI-TUSSIVE AGENTS

BACKGROUND OF THE INVENTION

The present invention relates to the use of GABA-B selective agonists in treating cough in mammals.

Gamma amino butryic acid (GABA) is a ubiquitous inhibitory neurotransmitter in the CNS and peripheral nervous systems (F. E. Bloom. Neurohumoral Transmission and the central nervous system. *The Pharmacological Basis of Therapeutics*, 7th Ed. (A. G. Gilman, L. S. Goodman, T. W. Rall and F. Murad, eds), MacMillan Publishing, N.Y., 1985, p. 250.). Evidence strongly suggests that GABA mediates the inhibitory actions of local interneurons in the brain and also mediates presynaptic inhibitory effects within the spinal cord. GABA appears to bind to at least two distinct types of receptors. Of these, GABA-A receptors have been well characterized and are coupled to chloride channels (J. Bormann. Electrophysiology of GABA-A and GABA-B receptor subtypes. *Trends Neurosci.*, 11, 112–116, 1988.). It is to these GABA-A receptors that benzodiazepines bind and exert anticonvulsant and anxiolytic effects through a facilitation of the action of GABA (E. Costa. Polytypic signalling at GABAergic synapses. *Life Sci.*, 42, 1407–1417, 1988.). These receptors can be selectively blocked with convulsant agents such as bicuculline. In contrast, GABA-B receptors are less well understood, although baclofen is a specific agonist at these bicuculline-insensitive receptors (N. Bowery. GABA-B receptors and their significance in mammalian pharmacology. *TIPS Revies*, 10, 401–407, 1989, and N. G. Bowery, A. Doble, D. R. Hill, A. L. Hudson, J. S. Shaw, M. J. Turnball and R. Warrington. Bicuculline-insensitive GABA receptor on peripheral autonomic nerve terminals. *Eur. J. Pharmac.*, 71, 53–70, 1981.). It now appears that GABA-B receptors are coupled to either calcium or potassium channels (J. Bormann. Electrophysiology of GABA-A and GABA-B receptor subtypes. *Trends Neurosci.*, 11, 112–116, 1988.).

GABA-B selective agents may not elicit the side effects associated with selective or non-selective activation of GABA-A receptors. For example, benzodiazepines facilitate responses at GABA-A receptors and produce troublesome side-effects of motor-incoordination, confusion, light-headedness and other adverse psychomotor and psychological effects (S. C. Harvey. Hypnotics and sedatives. *The Pharmacological Basis of Therapeutics*, 7th Ed. (A. G. Gilman, L. S. Goodman, T. W. Rall and F. Murad, eds), MacMillan Publishing, N.Y., 1985, pp. 349–350.).

Nosálová et al. recently described an antitussive effect for gabalinoleamide, a non-selective agonist at GABA receptors (G. Nosálová, D. Varonos, Z. Papadopouloû-Daipotis, P. Visnovsky and A. Strapkova. GABAergic mechanisms in the central control of cough. *Acta Physiologica Hungarica*, 70, 189–194, 1987.). They relate the antitussive and respiratory depressant effect of gabalinoleamide to an action at GABA-A receptors because similar effects are mentioned with respect to muscimol, a selective GABA-A agonist.

SUMMARY OF THE INVENTION

We have now unexpectedly discovered that GABA-B selective agonists such as baclofen have surprising activity as antitussive agents. Thus, we have discovered a method for treating cough in mammal which avoids the possible side effects caused by GABA-A agonism as described above by administering to said mammal an antitussive effective amount of a GABA-B selective agonist. The GABA-B selective agonist is preferably administered at a dose of from about 0.1 mg/kg to about 100 mg/kg, more preferably, from about 0.3 mg/kg to about 25 mg/kg. The GABA-B selective agonist is preferably baclofen.

DETAILED DESCRIPTION OF THE INVENTION

Figure 1:
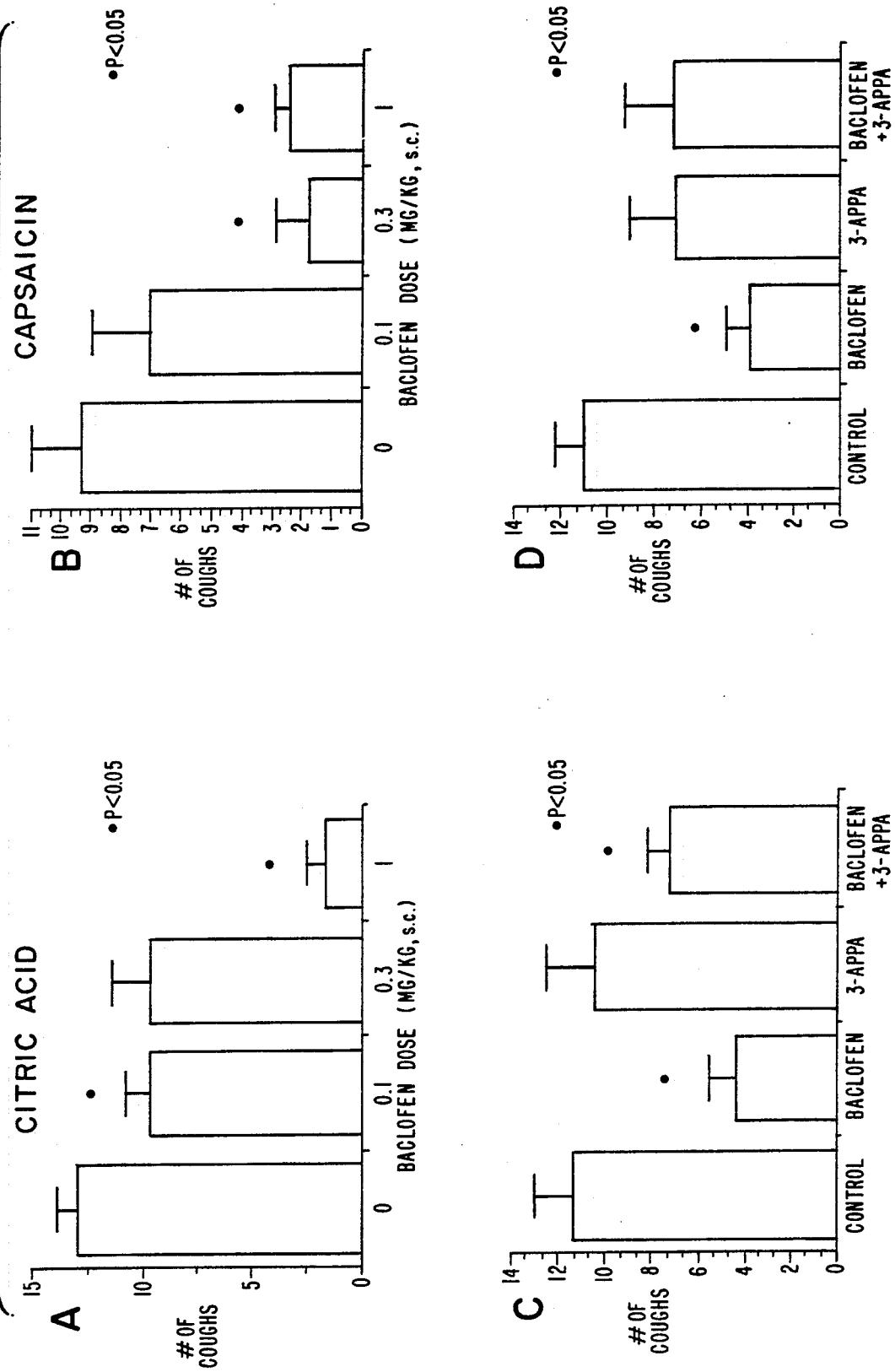
FIG. 1A is a bar graph showing the suppressing effect of increasing doses of baclofen on the number of coughs in the citric acid/guinea pig protocol described below.
FIG. 1B is a bar graph showing the suppressing effect of increasing doses of baclofen on the number of coughs in the capsaicin/guinea pig protocol described below.
FIG. 1C is a bar graph showing the effect on the number of coughs of a control, of baclofen, of 3-aminopropylphosphonic acid (3-APPA), and of baclofen after pre-treatment with 3-APPA in the citric acid/guinea pig protocol described below.
FIG. 1D is a bar graph showing the effect on the number of coughs of a control, of baclofen, of 3-APPA, and of baclofen after pretreatment with 3-APPA in the capsaicin/guinea pig protocol described below.

The method of the present invention can employ any GABA-B selective agonist. Examples of suitable GABA-B selective agonists include baclofen and 3-aminopropylphosphinic acid. With regard to the latter compound see J. M. Hills, et al., 3-Aminopropylphosphinic acid, a potent, selective GABA-B receptor agonist in the guinea pig ileum and rat anococcygeus muscle., *Br. J. Pharmac.*, 97, 1292-1296, 1989. The (±) form of baclofen has demonstrated cough suppressing activity significantly (about 14 to 40 times) better than codeine in our tests. Baclofen has the structural formula:

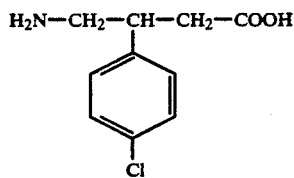

The (−) form of baclofen is preferred, since studies by others have demonstrated that this form is even more selective for GABA-B receptors.

The preferred GABA-B agonists are those agents which bind to GABA receptors that are bicuculline-insensitive (bicuculline is a known GABA-A selective antagonist) and which demonstrate GABA-B agonism in the inhibition of the twitch response in mouse vas deferens assay as described in Hughes et al., *Br. J. Pharmac.*, 53, 371-381, 1975. See also Hill et al., *Nature*, 290, 149-152, 1981 where the results in rat vas deferens are described in Table 1 thereof for baclofen and other compounds. Thus, a GABA agonist which is not blocked by the receptor binding of bicuculline is a GABA-B selective agonist.

Preferably, the GABA-B selective agonist will have an $IC_{50}$ of lower than about 100 μM, more preferably lower than about 50 μM, and most preferably lower than about 10 μM in the above described Hughes et al. mouse vas deferens assay. (±) Baclofen shows an $IC_{50}$ of about 3 μM in the rat vas deferens assay described by Hill et al. Preferably, the selective GABA-B agonists employed in the present invention will also exhibit a GABA-A to GABA-B binding ratio ($IC_{50}$ GABA-A binding/$IC_{50}$ GABA-B binding) of at least about 50, more preferably at least about 100, most preferably at least about 250, in the rat brain membrane binding assay described on pages 192-193 in Bowery et al., *Br. J. Pharmac.*, 78, 191-206, 1983. (−) Baclofen and (±) baclofen showed $IC_{50}$ GABA-A/$IC_{50}$ GABA-B binding ratios in such assay of greater than 2300 and greater than 550, respectively. See Table 2 on page 199 of the Bowery et al. article.

When used orally, parenterally or topically for the treatment of cough, the GABA-B selective agonists such as baclofen can be administered in an amount ranging from about 0.1 mg/kg body weight to about 100 mg/kg body weight, preferably from about 0.3 mg/kg body weight to about 25 mg/kg body weight per day. A typical recommended dosage regimen is oral administration of from 5 mg/day to 5000 mg/day, preferably 10 mg/day to 1000 mg/day, in two to four divided doses to achieve relief of the cough.

Determination of the proper dosage of a GABA-B selective agonist for a particular situation is within the skill of the art. Generally, treatment is initiated with smaller dosages that are less than the optimum dose of the compound. Thereafter, the dosage is increased by small increments until the optimum effect under the circumstances is reached. For convenience, the total daily dosage may be divided and administered in portions during the day if desired. The amount and frequency of administration of the GABA-B selective agonists will be regulated according to the judgment of the attending clinician considering such factors as age, condition and size of the patient as well as severity of the symptom being treated.

Administration of the dose can be intravenous, oral inhalation, parenteral, oral, subcutaneous, intramuscular, transdermal or any other acceptable method. The compounds of the present invention can be administered in any number of conventional dosage forms. Solid dosage forms include capsules, tablets, pills, powders, suspensions, solutions, cachets or suppositories. Parenteral preparations include sterile solutions or suspensions. Inhalation administration can be in the form of a oral spray, or by insufflation. Transdermal devices of the conventional reservoir or matrix patch type and the like can be employed also.

The formulations and pharmaceutical compositions contemplated by the above dosage forms can be prepared with conventional pharamaceutically acceptable excipients and additives, using conventional techniques. Such pharmaceutically acceptable excipients and additives include carriers, binders, flavorings, buffers, thickeners, color agents, dispersing agents, suspending agents, perfumes, preservatives, lubricants, etc.

The method of the invention may be demonstrated by the following proctocols in which baclofen refers to the (±) form of the compound:

Cough Models

1. Experiments on cough in guinea pigs

Unanesthetized male Dunkin Hartley guinea pigs (250-600 g) are placed into transparent plexiglas chambers and exposed to aerosols of capsaicin (300 μM), citric acid (0.55M), or their vehicles at an airflow of 4 L/min. Citric acid is dissolved in 0.9% saline vehicle and capsaicin is dissolved in 10% ethanol, 90% saline vehicle. The volume of solution aerosolized every minute is approximately 0.4 ml. The animals are first exposed to a vehicle aerosol for 4 minutes and then are exposed to citric acid or capsaicin aerosol for an additional 4 minutes. Coughing is detected by a microphone that is placed in the chamber and connected to an audio monitor and chart recorder. Coughs produced deflections on the chart paper which are later counted to determine a cough frequency. Test compounds are administered subcutaneously prior to exposure to citric acid or capsaicin. For studies involving baclofen alone, baclofen or vehicle are injected 60 minutes before exposure to the citric acid or capsaicin. For drug combination studies, 3-APPA is given 45 minutes before exposure to the antitussive agents such as baclofen and followed by citric acid or capsaicin 15 minutes after baclofen. All statistics are expressed relative to control values (unpaired t-test). The results are shown in FIGS. 1A, 1B, 1C and 1D and are discussed below.

Figure 3:
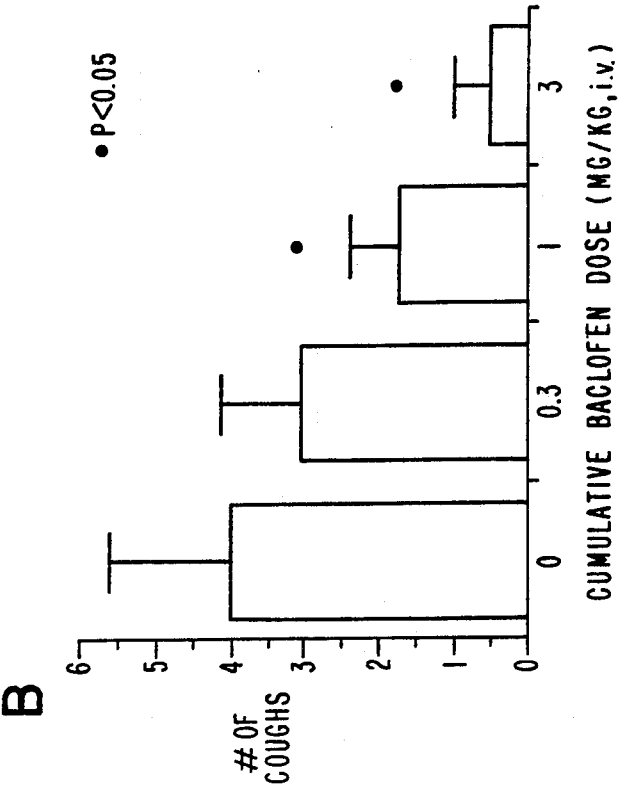
FIG. 3A is a bar graph showing the suppressing effect of a cumulative dose of baclofen on the number of coughs in the mechanically-induced cough in cats protocol described below.
FIG. 3B is a bar graph showing the suppressing effect of a cumulative dose of baclofen on the number of coughs in the electrically-induced cough in cats protocol described below.
Figure 3:
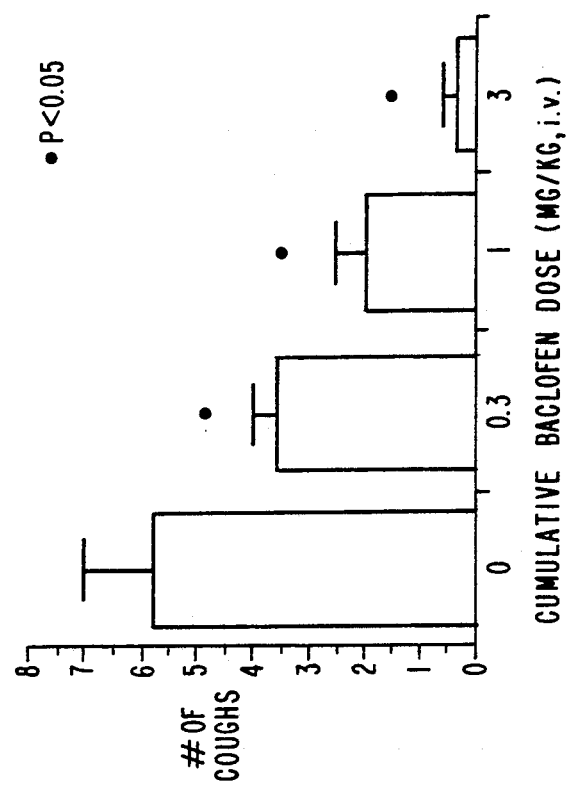

The responses in the citric acid model and capsaicin model to increasing doses of baclofen alone are shown in FIGS. 1A and 1B, respectively. The responses in the citric acid model and capsaicin model to a control, to baclofen alone (1.0 mg/kg, s.c.), to 3-APPA (10 mg/kg, s.c.) alone and to baclofen preceded by 3-APPA treatment are shown in FIGS. 1C and 1D, respectively. The data in FIGS. 1A and 1B represent values taken 1 hour following baclofen treatment. In FIGS. 1C and 1D, 3-APPA or vehicle was administered 45 minutes prior to data collection. Baclofen or vehicle was administered 15 minutes following 3-APPA.

2. Experiments on cough in cats

Cats (2.2-3.5 kg) are anesthetized with sodium pentobarbital (35 mg/kg, i.p.). Supplemental anesthetic (5 mg/kg, i.v.) is administered as required. Cannulas are placed in a femoral vein and artery for administering drugs and measuring arterial blood pressure, respectively. A tracheostomy is performed.

Electromyograms (EMGs) of respiratory muscle activity are recorded via bipolar silver wire electrodes placed in the diaphragm and rectus abdominus muscles by the technique of Basmajian and Stecko (1962). The EMGs are amplified (1000-2000×), filtered (500 Hz-10 KHz), monitored on an oscilloscope, and integrated with a "Leaky" RC circuit (100 ms time constant). These signals are displayed along with blood pressure on a chart recorder.

Coughing is elicited by probing the intrathoracic trachea with a flexible cannula (probe) and by electrical stimulation (2.2-10 V, 1 ms, 10 Hz, 10 strain) of the central cut end of the superior laryngeal nerve (SLN). These stimuli only elicit coughs, apneas, apneusis, or augmented breaths (sighs).

Coughing is produced by coordinated bursts of activity in inspiratory and expiratory muscles. We define a cough as a burst of activity at least 50% greater than control levels in the diaphragm (inspiratory muscle) immediately followed by or coincident with a burst of activity in the rectus abdominus muscle (expiratory muscle). These criteria eliminate apneas or apneusis (no inspiratory or expiratory bursts) and augmented breaths (no expiratory muscle activity). Test compounds are administered intravenously to determine their effects on mechanically (probe) and electrically (SLN) induced cough. For studies involving baclofen alone, cumulative doses of baclofen or vehicle are injected 5 minutes before the induction of a cough response. For drug combination studies, 3-APPA (3 mg/kg, i.v.) is given 5 minutes before the induction of cough. Baclofen (0.7 mg/kg, i.v.) is immediately administered after collection of data for 3-APPA and followed 5 minutes later by the induction of cough. All statistics are expressed relative to control values (paired t-test). The results are shown in FIGS. 2A, 2B 2C, 2D, 3A and 3B and are discussed below.

A representative experiment is shown in FIGS. 2A-2D. The top trace in FIGS. 2A-2D shows integrated rectus abdominus (expiratory muscle) activity. The bottom trace in FIGS. 2A-2D shows integrated diaphragm (inspiratory muscle) activity. FIGS. 2A and 2B represent control cough responses to mechanical and electrical stimulus, respectively. FIGS. 2C and 2D depict responses to mechanical and electrical stimulus 5 minutes following 0.7 mg/kg, i.v. of baclofen.

In FIGS. 3A and 3B, data from all animals is shown. Data were collected 5 minutes following i.v. injection of baclofen.

RESULTS

1. Citric acid and capsaicin-induced cough in guinea pigs

Guinea pigs were exposed to citric acid at a concentration of 0.55M. This dose of citric acid produced cough frequencies of 10-13 per exposure. The dose of capsaicin used was 0.3 mM and this dose produced cough frequencies of 7-9 per exposure. These doses produced consistent responses and were well tolerated by the animals. Larger doses (up to 2M for citric acid and 3 mM for capsaicin) produced distress to the animals. Lower doses (to 0.2M for citric acid and 0.03 mM for capsaicin) produced inconsistent cough responses.

The GABA-B agonist baclofen produced a dose-dependent reduction in cough frequency in both models (FIG. 1A, B). Codeine reduced cough frequency in both the citric acid ($ED_{50}=30$ mg/kg) and capsaicin ($ED_{50}=10$ mg/kg) cough models. Baclofen was approximately 40 times more potent than codeine in the citric acid model and 14 times more potent than codeine in the capsaicin model (ED50 for baclofen approximately 0.7 mg/kg for both models). These effects of baclofen were attenuated by prior treatment with the GABA-B antagonist 3-aminopropylphosphonic acid (3-APPA, FIGS. 1C, D). 3-APPA is a known GABA-B antagonist (Kerr, D. I. B., J. Ong., G. A. R. Johnston, and R. H. Prager. GABA-B-receptor-mediated actions of baclofen in rat isolated neocortical slice preparations: antagonism by phosphonoanalogues of GABA. *Brain Res.* 480: 312-316, 1989).

2. Mechanically and electrically-induced cough in cats

Mechanically-induced cough reproducibly produced from 5-7 coughs per trial throughout the course of an experiment (usually 2-3 hours). An example of the changes in integrated diaphragm and rectus abdominus muscle activity during coughing elicited by probing the intrathoracic trachea is shown in FIG. 2A. The coughing episode consisted of very large bursts in the activities of these muscles relative to baseline discharge.

Coughing produced by electrical stimulation of the superior laryngeal nerve was similar to that produced by mechanical stimuli (FIG. 2B). However, the number of coughs produced per episode was not as great (3-5 coughs per trial).

Figure 2:
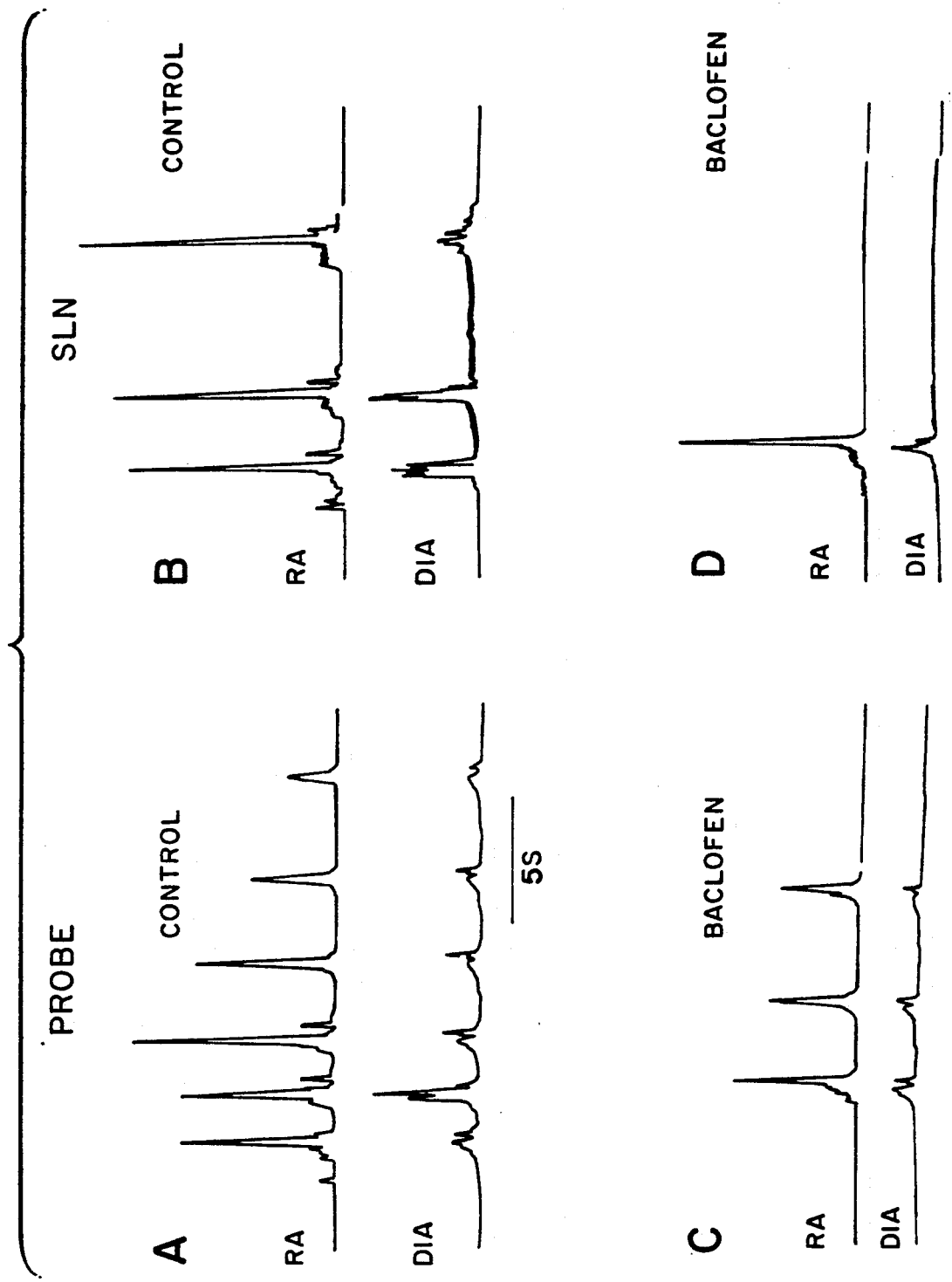
FIG. 2A is an electromyographic tracing showing the effect on integrated rectus abdominus (expiratory muscle) activity (top tracing) and on integrated diaphragm (inspiratory muscle) activity (bottom tracing) of treatment with control in the mechanically-induced cough in cats protocol described below.
FIG. 2B is an electromyographic tracing showing the effect on integrated rectus abdominus (expiratory muscle) activity (top tracing) and on integrated diaphragm (inspiratory muscle) activity (bottom tracing) of treatment with control in the electrically-induced cough in cats protocol described below.
FIG. 2C is an electromyographic tracing showing the effect on integrated rectus abdominus (expiratory muscle) activity (top tracing) and on integrated diaphragm (inspiratory muscle) activity (bottom tracing) of treatment with baclofen in the mechanically-induced cough in cats protocol described below.
FIG. 2D is an electromyographic tracing showing the effect on integrated rectus abdominus (expiratory muscle) activity (top tracing) and on integrated diaphragm (inspiratory muscle) activity (bottom tracing) of treatment with baclofen in the electrically-induced cough in cats protocol described below.

FIG. 2 also shows the effect of baclofen on mechanically and electrically-induced coughing. Examples of the effect of baclofen on single trial cough responses to mechanical (FIG. 2A control, FIG. 2C after baclofen) and electrical stimuli (FIG. 2B control, FIG. 2D after baclofen) are shown. The inhibitory effect of baclofen on coughing produced by both types of stimuli was dose-dependent (FIGS. 3A, 3B).

The GABA-B selective agonist baclofen reduced cough in a dose-dependent manner in the citric acid cough model, the capsaicin cough model, and the cat cough models. Because 3-APPA attenuated these responses, these results strongly indicate that GABA-B receptors can inhibit chemically, mechanically, and electrically-induced cough. Furthermore, because cough was inhibited in both guinea pigs and cats, the antitussive activity of the GABA-B selective agonist baclofen is applicable to multiple mammalian species.

The following formulations exemplify some of the dosage forms of the compositions of this invention. In each, the term "active compound" refers to baclofen. However, this compound may be replaced by equally effective amounts of other GABA-B selective agonists.

EXAMPLE A

| No. | Ingredients | Tablets mg/tablet | mg/tablet |
|---|---|---|---|
| 1. | Active compound | 5 | 20 |
| 2. | Lactose USP | 122 | 113 |
| 3. | Corn Starch, Food Grade, as a 10% paste in | 30 | 40 |

-continued

| No. | Ingredients | Tablets mg/tablet | mg/tablet |
|---|---|---|---|
| | Purified Water | | |
| 4. | Corn Starch, Food Grade | 45 | 40 |
| 5. | Magnesium Stearate | 3 | 7 |
| | Total | 205 | 220 |

Method of Manufacture

Mix Item Nos. 1 and 2 in a suitable mixer for 10–15 minutes. Granulate the mixture with Item No. 3. Mill the damp granules through a coarse screen (e.g., $\frac{1}{4}''$, 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A method for treating cough in a mammal comprising administering to said mammal an anti-tussive effective amount of a GABA-B selective agonist.

2. A method according to claim 1, wherein the GABA-B selective agonist is administered at a dose of from about 0.1 mg/kg to about 100 mg/kg.

3. A method according to claim 1, wherein the GABA-B selective agonist is baclofen.

4. A method according to claim 3, wherein baclofen is administered at a dose of from about 0.3 mg/kg to about 25 mg/kg.

5. A method according the claim 1, wherein the GABA-B selective agonist is 3-aminopropylphosphinic acid.

* * * * *